United States Patent [19]

Tremaine

[11] Patent Number: 5,178,415
[45] Date of Patent: Jan. 12, 1993

[54] FINGERPRINT CARD HOLDER ASSEMBLY

[76] Inventor: David K. Tremaine, 4055 Hamilton, #8, P.O. Box 4556, San Diego, Calif. 92164

[21] Appl. No.: 716,682

[22] Filed: Jun. 17, 1991

[51] Int. Cl.$^5$ .............................................. B42D 3/00
[52] U.S. Cl. .................................. 281/45; 118/31.5; 118/500; 118/503; 427/1
[58] Field of Search ................. 281/45; 118/31.5, 500, 118/503; 427/1; 283/68

[56] References Cited

U.S. PATENT DOCUMENTS

| | | | |
|---|---|---|---|
| 1,251,113 | 12/1917 | Ryan | 118/31.5 |
| 2,297,066 | 9/1942 | Miller | 281/45 |
| 3,318,282 | 5/1967 | Bean | 427/1 X |
| 4,281,616 | 8/1981 | Le Vantine | 427/1 |

Primary Examiner—P. W. Echols
Assistant Examiner—Willmon Fridie, Jr.
Attorney, Agent, or Firm—Charles C. Logan, II

[57] ABSTRACT

A fingerprint card holder assembly to be used with fingerprint cards having a layer of transparent adhesive material on their front surface where a person's individual fingerprints are received and recorded. The fingerprint card holder assembly has a base mounted on a support platform. A fingerprint card guide is mounted on the top surface of the base for aligning the fingerprint card. A fingerprint card locking unit is pivotally mounted on the base and it pivots from an upright position to a horizontal position that locks a fingerprint card against the top surface of the base. There is structure on the bottom surface of the fingerprint card guide and also on the rear surface of the fingerprint card locking unit to prevent the adhesive on the top surface of the fingerprint card from sticking to either of these respective members when the fingerprint card holder assembly is being used.

6 Claims, 1 Drawing Sheet

U.S. Patent　　Jan. 12, 1993　　5,178,415
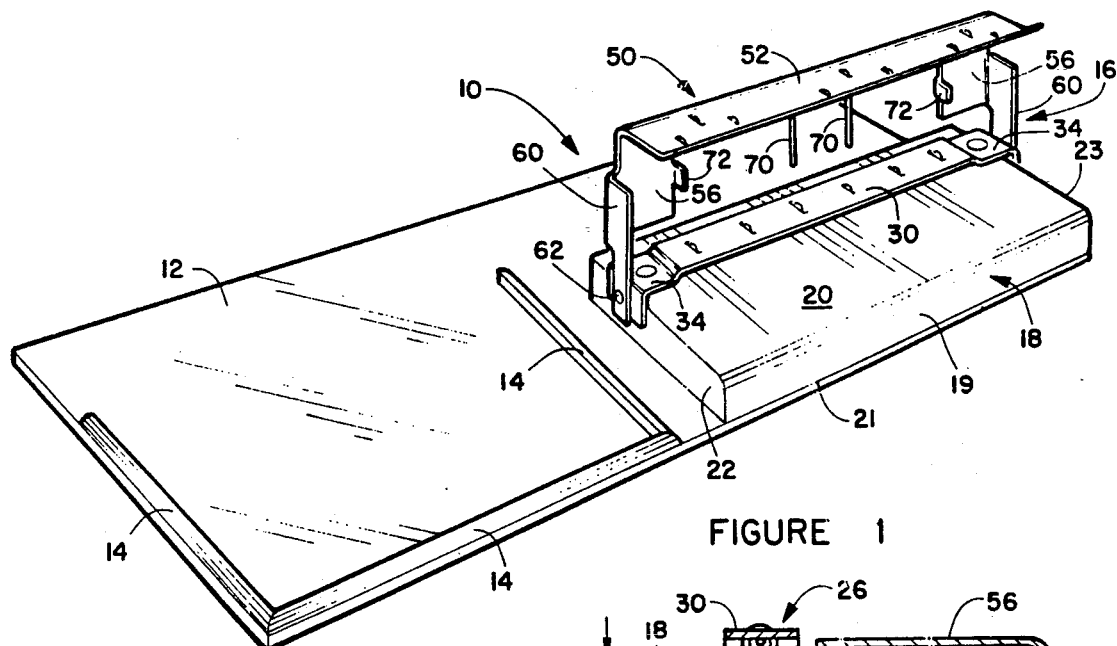
FIGURE 1
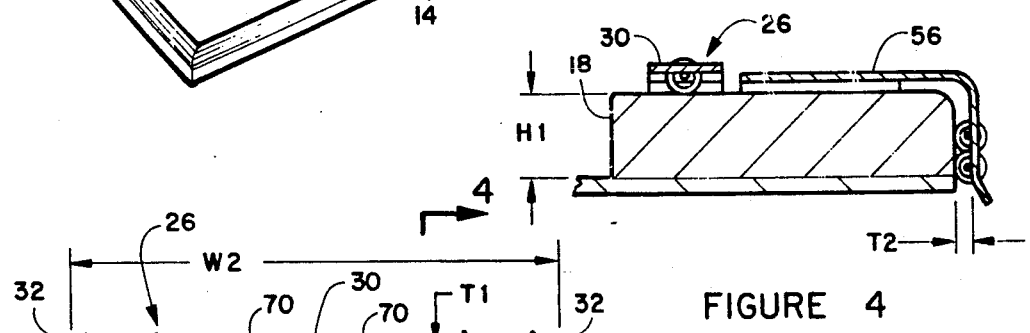
FIGURE 2
FIGURE 4
FIGURE 5
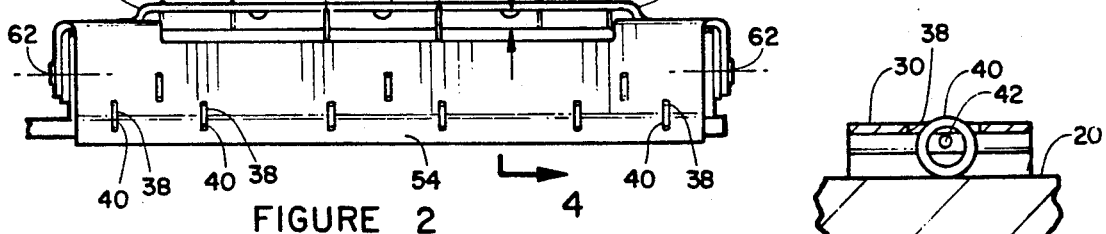
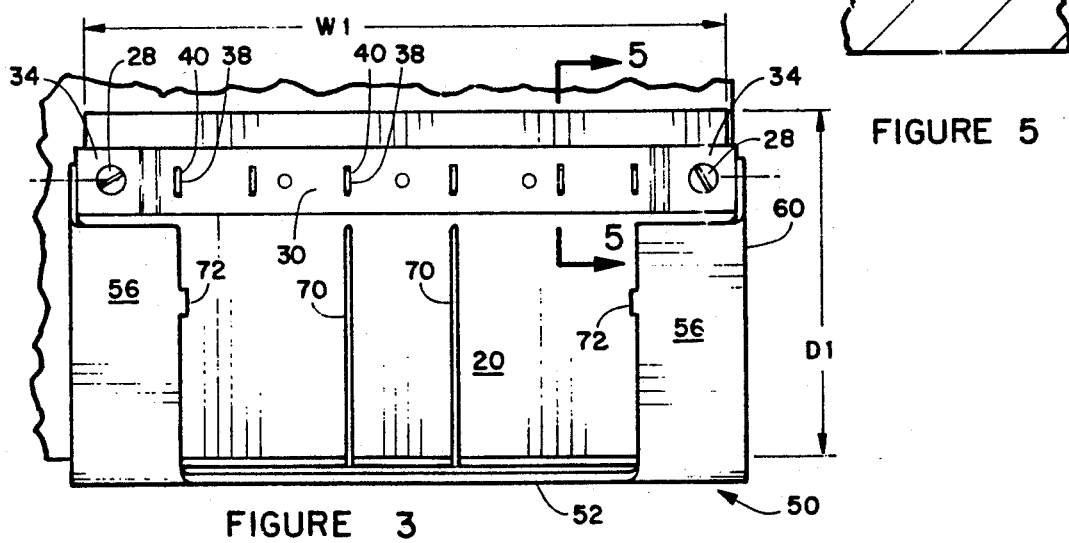
FIGURE 3

FINGERPRINT CARD HOLDER ASSEMBLY

BACKGROUND OF THE INVENTION

The invention relates to fingerprinting and more specifically to a fingerprint card holder assembly.

Presently police departments and other government agencies utilize the same or very similar fingerprint cards. These cards have a heading portion and a fingerprint portion. The fingerprint portion usually consists of three transversely extending rows. These rows are broken up into frames for receiving the individual fingerprints of the respective fingers of the left and right hands of an individual. The bottom row is divided into frames that receive imprints of the fingers taken simultaneously together.

The process for fingerprinting an individual requires that the individual have ink applied to their fingertips and then the finger is pressed downwardly into its identified frame with a rolling motion to give a complete imprint thereof. The ink utilized for making the fingerprints normally takes at least a half hour to dry. As a result, the fingerprints on the cards can be smudged very easily if proper care is not taken to prevent them from being touched before they are completely dry. Sometimes this means that a new set of fingerprints must be taken and this results in an unecessary waste of the police personnel's time.

In the Tremaine U.S. Pat. No. 5,013,071, a unique improved fingerprinting system is disclosed and incorporated into this patent application by reference. His fingerprinting system takes a standard fingerprint card and he applies an adhesive to the top surface of the fingerprint portion of the card. The card with its exposed adhesive on its top surface is inserted into a fingerprint card holder and sequentially advanced so that the respective rows can have fingerprints applied to the individual frames therein. A problem exists when using a fingerprint card such as Tremaine's when used with a conventional state of the art fingerprint card holder. The top surface of the card tends to stick to the underside surface of the fingerprint card guide and also to the rear surface of the fingerprint card locking unit. It is then necessary to use unproductive time to free the fingerprint card and sometimes the endeavor results in messing up some of the prints on the card.

It is an object of the invention to provide a novel fingerprint card holder assembly that can be used with the novel fingerprinting system described in Tremaine's U.S. Pat. No. 5,013,017.

It is also an object of the invention to provide a novel fingerprint card holder assembly that is economical to manufacture and market.

It is an additional object of the invention to provide a novel fingerprint card holder assembly that is easy to use.

SUMMARY OF THE INVENTION

The novel fingerprint card holder assembly has been designed to be used with fingerprint cards having an adhesive coating on the top surface of their fingerprint portion. These fingerprint cards and the unique fingerprinting system is described in U.S. Pat. No. 5,013,071.

The fingerprint card having the adhesive coating on its top surface is inserted into the novel fingerprint card holder assembly in the same manner as was standard with previous fingerprint card holders. Due to the increased spacing between the top surface of the base and the addition of freely rotatable rings (rollers, loops, washers and other like structures can be used) on the bottom surface of the transversely extending fingerprint card guide, the adhesive on the card does not stick to the underside of the fingerprint card guide as it is passed therebeneath when advancing the fingerprint card to the next row onto which fingerprints would be received. The fingerprint card locking unit also has a plurality of freely rotatable rings secured to the rear surface of its front cross member which spaces the sticky adhesive surface of the fingerprint card from the rear surface of the front cross member of the fingerprint card locking unit. As the fingerprint card is advanced to the next row, the freely rotating rings will prevent any sticking of the top surface of the card to the fingerprint card locking unit.

DESCRIPTION OF THE DRAWING

FIG. 1 is a front perspective view of the novel fingerprint card holder assembly;

FIG. 2 is a front elevation view of the fingerprint card holder;

FIG. 3 is a top plan view of the fingerprint card holder;

FIG. 4 is a cross sectional view taken along lines 4—4 of FIG. 3; and

FIG. 5 is a cross sectional view showing the manner in which the freely rotatable rings prevent the adhesive on the top surface of the fingerprint card from sticking to the underside of the cross member portion.

DESCRIPTION OF THE PREFERRED EMBODIMENT

The novel fingerprint card holder assembly will now be described by referring to FIGS. 1-5 of the drawing. The fingerprint card holder assembly is generally designated numeral 10. It has a transversely extending support panel 12 having a fingerprint card frame 14 mounted on its top surface to hold the fingerprint card while a transparent plastic cover sheet is applied to the top surface of the fingerprint card. A fingerprint card holder 16 is also mounted on its top surface to hold the fingerprint card while a transparent plastic cover sheet is applied to the top surface of the fingerprint card.

Fingerprint card holder 16 is formed from a base 18 having a front wall 19, a top wall 20, a bottom wall 21, a left side wall 22, and a right side wall 23.

A fingerprint card guide 26 is mounted to the top wall 20 by screws 28. Fingerprint card guide 26 has a cross member portion 30 having downwardly extending web portions 32 at each of its opposite ends. Attachment legs 34 are connected to the respective web portions. Flanges 36 extend downwardly over the respective side walls 22 and 23. A plurality of slots 38 receive a portion of rings 40 that are freely rotated on pins 42 secured to the cross member portion 30. These slots and rollers are aligned so that they track with the preprinted lines on the top surface of the fingerprint card that divides its rows into individual frames for a single fingerprint.

Fingerprint card locking unit 50 has a front cross member 52 having a downwardly and outwardly extending front lip 54 at its lower edge. A plurality of slots 38 have rings 40 mounted on pins 42 to prevent the adhesive coating on the top of the fingerprint card from sticking to the front cross member 52. Extending transversely to front cross member 52 at its opposite ends are panel sections 56. Pivot arms 60 have their one end secured to panel sections 56 and their other end is pivotally secured by hinge pins 62 to flanges 36 and the side walls of base 18. A plurality of fingerprint card hold down arms 70 function to prevent the fingerprint card from arching upwardly when it is locked in place by fingerprint card locking unit 50. Legs 72 also press downwardly on the top surface of the fingerprint card to hold it against the top wall 20 of base 18.

What is claimed is:

1. A fingerprint card holder assembly comprising:
   a transversely extending elongated base having a predetermined width W1, a predetermined depth D1, and a predetermined height H1, said base having a front wall, a top wall, a bottom wall and laterally spaced left and right side walls;
   a transversely extending elongated fingerprint card guide that extends across the width W1 of said base, said fingerprint card guide having a cross member portion whose length W2 is slightly larger than the width of a fingerprint card, the opposite ends of said cross member are connected to downwardly extending web portions that are each in turn connected to attachment leg portions that are each secured to the top surface of said base and said cross member portion is spaced a predetermined height T1 above the top surface of said base;
   a plurality of freely rotating rings attached to the bottom surface of the cross member portion of said fingerprint card guide;
   a transversely extending elongated fingerprint card locking unit having a vertically extending front cross member that extends across the width W1 of said base, a horizontal left side panel section and a horizontal right side panel section are connected to said front cross member adjacent its opposite ends, a left side pivot arm and a right side pivot arm are connected to the respective left and right side panel sections; and
   means for pivotally securing the respective pivot arms of said fingerprint locking unit to said base so that it can be pivoted between a horizontal locking position and an upright unlocked position.

2. A fingerprint card holder assembly as recited in claim 1 wherein said base has its bottom wall attached to the top surface of a support panel.

3. A fingerprint card holder assembly as recited in claim 2 further comprising a three sided frame mounted on the top surface of said support panel.

4. A fingerprint card holder assembly as recited in claim 1 further comprising means extending between the fingerprint card guide and the front cross member of the fingerprint card locking unit for pressing downwardly on the top surface of a fingerprint card.

5. A fingerprint card holder assembly comprising:
   a transversely extending elongated base having a predetermined width W1, a predetermined depth D1, and a predetermined height H1, said base having a front wall, a top wall, a bottom wall and laterally spaced left and right side walls;
   a transversely extending elongated fingerprint card guide that extends across the width W1 of said base, said fingerprint card guide having a cross member portion whose length W2 is slightly larger than the width of a fingerprint card, the opposite ends of said cross member are connected to downwardly extending web portions that are each in turn connected to attachment leg portions that are each secured to the top surface of said base and said cross member portion is spaced a predetermined height T1 above the top surface of said base;
   a transversely extending elongated fingerprint card locking unit having a vertically extending front cross member that extends across the width W1 of said base, a horizontal left side panel section and a horizontal right side panel section are connected to said front across member adjacent its opposite ends, a left side pivot arm and a right side pivot arm are connected to the respective left and right side panel sections;
   a plurality of freely rotating rings attached to the rear surface of the front cross member of said fingerprint and card locking unit; and
   means for pivotally securing the respective pivot arms of said fingerprint locking unit to said base so that it can be pivoted between a horizontal locking position and an upright unlocked position.

6. A fingerprint card holder assembly comprising:
   a transversely extending elongated base having a predetermined width W1, a predetermined depth D1, and a predetermined height H1, said base having a front wall, a top wall, a bottom wall and laterally spaced left and right side walls;
   a transversely extending elongated fingerprint card guide that extends across the width W1 of said base, said fingerprint card guide having a cross member portion whose length W2 is slightly larger than the width of a fingerprint card, the opposite ends of said cross member are connected to downwardly extending web portions that are each in turn connected to attachment leg portions that are each secured to the top surface of said base and said cross member portion is spaced a predetermined height T1 above the top surface of said base;
   a transversely extending elongated fingerprint card locking unit having a vertically extending front cross member that extends across the width W1 of said base, a horizontal left side panel section and a horizontal right side panel section are connected to said front cross member adjacent its opposite ends, a left side pivot arm and a right side pivot arm are connected to the respective left and right side panel sections;
   a downwardly and forwardly extending lip on the bottom edge of the front cross member of said fingerprint card locking unit, a plurality of freely rotating rings attached to the rear surface of the lip extending downwardly and forwardly from said front cross member; and
   means for pivotally securing the respective pivot arms of said fingerprint locking unit to said base so that it can be pivoted between a horizontal locking position and an upright unlocked position.

* * * * *